United States Patent [19]

Morgan et al.

[11] Patent Number: 6,146,688

[45] Date of Patent: *Nov. 14, 2000

[54] METHOD OF CREATING A BIOSTATIC AGENT USING INTERPENETRATING NETWORK POLYMERS

[76] Inventors: Harry C. Morgan, Lower Level, Two Gateway Center, Pittsburgh, Pa. 15222; Joseph F. Meier, 2375 Harrison City Rd., Export, Pa. 15632; Robert L. Merker, 124 Sebald La., Pittsburgh, Pa. 15237

[ * ] Notice: This patent issued on a continued prosecution application filed under 37 CFR 1.53(d), and is subject to the twenty year patent term provisions of 35 U.S.C. 154(a)(2).

[21] Appl. No.: 08/996,749

[22] Filed: Dec. 23, 1997

[51] Int. Cl.$^7$ ......................................................... B05D 7/02
[52] U.S. Cl. ........................... 427/2.3; 427/2.28; 427/336; 427/393.5; 427/387
[58] Field of Search ..................................... 427/2.3, 2.28, 427/393.5, 336, 387; 604/265

[56] References Cited

U.S. PATENT DOCUMENTS

| | | | |
|---|---|---|---|
| 3,695,921 | 10/1972 | Shepherd et al. | 117/72 |
| 4,411,928 | 10/1983 | Baldwin | 427/2 |
| 4,605,564 | 8/1986 | Kulla et al. | 427/2 |
| 4,675,347 | 6/1987 | Mochizuki et al. | 523/122 |
| 4,847,088 | 7/1989 | Blank | 424/404 |
| 4,865,870 | 9/1989 | Hu et al. | 427/2 |
| 4,999,210 | 3/1991 | Soloman et al. | 427/2 |
| 5,053,048 | 10/1991 | Pinchuk | 623/1 |
| 5,069,899 | 12/1991 | Whitbourne et al. | 424/56 |
| 5,290,894 | 3/1994 | Melrose et al. | 526/315 |
| 5,624,704 | 4/1997 | Darouiche et al. | 427/2.24 |

*Primary Examiner*—Shrive Beck
*Assistant Examiner*—Jennifer L. Kolb

[57] ABSTRACT

Applicants' invention is a method for creating an interpenetrating network on the surface of devices and supplies that is biocompatible and antimicrobial. According to Applicants' invention, a polymerizable or monomeric quaternary ammonium salt in a solvent is exposed to a polymeric substrate. The quaternary salt in solvent is absorbed by the polymeric substrate and the quaternary salt is polymerized such that an interpenetrating network is formed with said polymeric substrate.

17 Claims, No Drawings

METHOD OF CREATING A BIOSTATIC AGENT USING INTERPENETRATING NETWORK POLYMERS

BACKGROUND

Quaternary ammonium salts have the general formula of:

$$[(CH_3)_4N]^+X^- \tag{1}$$

where X is a halogen such as iodine, chlorine or bromine. A variety of quaternary ammonium compounds are available and widely used as disinfectants and biocides and to treat items that may undesirably support microbial growth. For example, quaternary ammonium salts are used to treat carpeting, walls, various commercial products such as sponges and fabrics, and even water. They are also used to rehabilitate "sick buildings," particularly after floods and water leaks, and reduce odors caused by mildew, fungus and bacterial growth in damp basement areas.

Most quaternary ammonium salts commercially available are generally pre-packaged in water or alcohol solutions of approximately 2–3% or less quaternary salt concentration. They are applied to substrates such as carpets, walls, floors, to kill the bacteria. The method of application often relies on delivering the quaternary ammonium salt in a fine spray. When treating fabrics, sponges, bedding, and similar products, the concentration of the quaternary ammonium salts generally can be much lower, e.g., less than 1%.

Despite knowledge of the common usage of quaternary ammonium salts for imparting antimicrobial properties, a method was not known for treating medical devices and supplies and other consumer products that was biocompatible.

Applicants' method uses quaternary ammonium salts of the general formula of:

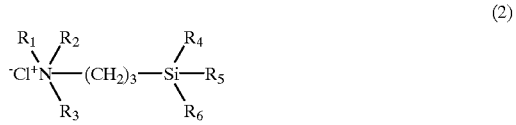

wherein $R_1$ and $R_2$ are methyl (—$CH_3$) groups; $R_3$ is octadecyl ($CH_3(CH_2)_{17}$—); and $R_4$, $R_5$ and $R_6$ are methoxy (—$OCH_3$) groups. Applicants' method can be used to treat, either during or after manufacture, textile materials, particularly medical devices and supplies, such that such devices and supplies have long-lasting, non-leaching, biocidal properties on the surface and are not toxic to the host organism. The treatment involves converting the methoxy groups to OH groups through hydrolysis and then polymerizing through condensation of the OH groups to form siloxane bonds and water.

More specifically, because catheter infections are the leading cause of hospital or long-term care infections, numerous attempts have been made to create a catheter that is antimicrobial. Most antimicrobial catheters rely on the impregnation of antibiotics to achieve a catheter that is resistant to bacterial infection. Unfortunately, this use of antibiotics results in increased resistance to antibiotics, a significant problem for immuno-compromised patients. It also leads to the subsequent long-term inefficacy of such catheters.

Further, some antimicrobial catheters use a coating treatment to provide a vehicle for entrapping drugs onto the catheter surface but permit subsequent diffusion into the biological environment. Many such treatments rely upon a polyurethane in a solvent to entrap antibiotic pharmaceutical agents.

Thus, despite numerous and concerted efforts, a cost-efficient method has not been devised to impart non-leaching, biocompatible, antimicrobial properties to surfaces. In particular, despite the long felt need for such method or device in the catheter industry, until Applicants' invention, no such method or device existed.

Interpenetrating polymer networks (IPNs) are well known in the art. They are prepared in a variety of ways and the technical literature is replete with the technology for the manufacture of such IPNs. The most common ways to create IPNs are (1) by blending two or more polymers in an internal mixer using temperature, mixing time and torque to obtain a blended or grafted IPN, and (2) by "swelling," i.e., expanding, a higher polymer with a monomer or a solution of a monomer and polymerizing the monomer to a polymer in situ.

In this latter case, when monomer (A) is polymerized to form a polymer (A) in a host or substrate polymer (B), such as silicone or polyurethane elastomer, a high degree of permanence can be established for polymer A. That is, polymer A can only be removed to a limited degree when the IPN is extracted by an organic solvent or water. Therefore, such an IPN has long term stability.

However, until now, IPNs of polymerized quaternary ammonium salt monomers have not been used to impregnate the surfaces of medical devices and supplies to impart antimicrobial properties to such devices and supplies. Applicants' technique accomplishes this in such a manner that does not compromise their biocompatibility.

It is an object of this invention to provide a method for creating an interpenetrating network on the surface of devices and supplies that is biocompatible and antimicrobial.

It is a further object of the invention to provide a method for creating a biocompatible and antimicrobial surface for consumer products.

It is an object of the invention to incorporate antimicrobial activity into devices that may be implanted in or used on living organisms.

It is a further object of the invention to provide an antimicrobial catheter that is not dependant on antibiotic drugs for antimicrobial activity.

It is an object of this invention to provide a process for creating a polymeric coating having antimicrobial properties that can be applied to various medical device and supply surfaces.

Other objects of the invention will be obvious upon reading the following specification and claims.

FIELD OF INVENTION

This invention relates to a novel way to treat surfaces such that they have a non-leaching antimicrobial property that is not dependant on antibiotic drugs. The method described herein may be used to prepare or treat biocompatible devices or other products and impart antimicrobial properties to surfaces through coatings containing the antimicrobial.

SUMMARY OF THE INVENTION

Applicants' method is a technique for impregnating a surface with quaternary salts that have antimicrobial characteristics and are polymerizable. Applicants' technique calls for the creation of an IPN of the quaternary salt in or on the material to be treated. In one embodiment of Applicants' method, the quaternary salt is polymerized after it has penetrated the surface of the host polymer, i.e., the polymer on the surface of the device or product to be treated. The depth of the penetration of the quaternary salt in the host polymer is controlled by the period of time that the polymeric substrate is exposed to the solution containing the quaternary salt, and solvent power, i.e., how much of the solvent is adsorbed by the subject device or product during the exposure period. The solvent power is reflected by the weight gain of the subject device or product during the exposure period.

After the quaternary salt monomer has been absorbed by the host polymer, the quaternary salt is polymerized to form an interpenetrating network polymer (IPN). Such polymerization preferably is achieved by using 0.1N NaOH, 0.1N HCl, heat or a combination thereof. The presence of the interpenetrating polymer (i.e., the active quaternary ammonium group) has been substantiated by a dye test using bromophenol blue. The longevity or permanence of the quaternary ammonium group has been demonstrated by dye testing the treated material after repeatedly challenging the treated host substrate with multiple hot (e.g., 140° F.) water rinses, aging treated samples with forced air or in a microwave oven, and subjecting the treated sample to repeated autoclave cycles (270° F. for 30 minutes).

As the following non-limiting examples show, the IPNs of silicone and polyurethane rubber, including silicone and polyurethane rubber catheters, treated according to Applicants' method, have been shown to possess the ability to kill bacteria, fungi and molds.

In other embodiments of Applicants' invention, a non-leaching antimicrobial IPN is created within the cavities and pores of the material to be treated. This embodiment does not require that the material to be treated be swelled. Rather, the quaternary salt monomer/solvent are absorbed into the pores, the solvent is evaporated and the monomer is polymerized within and through the pores of the substrate. In this manner the polymerized quaternary salt is "anchored" to the substrate through a physical interaction or blending. The level of quaternary salt polymer should be less than about 5% by weight on the substrate to minimize the decrease of air flow through the polymer substrate.

Another embodiment of Applicants' invention provides for the creation and application of a polymeric coating that can be applied to a variety of non-polymeric surfaces.

PREFERRED EMBODIMENTS

Applicants' method uses the technology of swelling a host polymer with a solvent solution of quaternary ammonium salt. Preferably, the solvent is selected based on its ability to swell rapidly the host polymer the desirable amount without significantly disrupting the integrity of the underlying host substrate. Even more preferably, the appropriate and necessary amount of swelling of the host substrate, e.g., as reflected by an approximately 20 to 50 percent weight gain of the solvent and quaternary salt, occurs within 10 minutes or less after exposure to the solvent. Even more preferably, the boiling point of the solvents are relatively low to facilitate the removal, i.e., the evaporation, of the solvent from the substrate being treated. The following non-limiting examples reflect application of Applicants' invention.

EXAMPLE ONE

Quaternary Ammonium Salt IPN Polymer on Thermoplastic Polyurethane Rubber Catheters (TPU)

Applicants' method was applied to a commercially available polyurethane rubber catheter, i.e., the host polymer. A solvent solution of quaternary ammonium salt was employed. Specifically, commercially available quaternary ammonium salt products were used that provided for different concentrations of a quaternary salt in methanol solution. The selected solvent was used to prepare 1–5% solutions of quaternary ammonium salt in ethyl acetate. This solvent was chosen because of its ability to rapidly induce the swelling of the underlying substrate polymer. The solvent in this example caused a thermoplastic polyurethane rubber catheter to exhibit approximately 30% weight gain in approximately 5 minutes. Such swelling was measured by weight gain attributed to the solvent and quaternary ammonium salt when compared with an untreated device or product. The catheter hub swelled slightly less than the catheter tube as the following Table 1 shows:

| Immersion Time in Ethyl Acetate 5% Quaternary Ammonium Salt, minutes | % wt. gain of TPU Catheter | % wt. gain Hub from Catheter |
|---|---|---|
| 1 | 16.8 | 8.7 |
| 2 | 15.4 | 13.8 |
| 5 | 30.8 | 20.8 |
| 10 | 40.5 | — |

This disparity in weight gain between the hub and the other portions of the catheter tube may be caused by the hub being thicker in cross section than the catheter tube or the hub being made of a different thermoplastic polyurethane.

After swelling in ethyl acetate, the swollen catheter was immersed in 0.1 NaOH to accelerate the polymerization of the quaternary ammonium salt. The clear 0.1N NaOH solution became slightly cloudy indicating that some of the monomeric quaternary ammonium salt was dissolved or leached from the surface of the catheter and polymerized in the 0.1N NaOH solution. However, a significant amount of polymerized quaternary ammonium salt remained on the surface and penetrated the catheter wall to a slight degree.

Standard Test A—Bromophenol Blue Testing

Successful treatment of the catheter was verified by exposing the treated catheter surface to bromophenol blue which colors the substrate blue in the presence of monomeric or polymeric quaternary ammonium salt. Additionally, a treated catheter segment was subjected to a 5×series of hot water rinses (140° F. tap water 200:1 on a shaker for 3 minutes) followed by a test with bromophenol blue. This sample also turned blue indicating that the IPN retained its activity and was not easily extracted. If desired, deeper penetration of the catheter wall can be achieved by increasing the immersion time or using a more powerful solvent. However, more powerful solvents or longer exposure time in the solvents, could result in a longer drying time to reduce the retained solvent content to acceptable levels. Further, the length of the exposure time must be calibrated for non-crosslinked polymers to ensure that the integrity of the underlying product or device to be treated is not compromised.

Standard Test B—Bio Testing of TPU Catheters

Catheters treated as described above, were submitted for and subjected to biotesting, i.e., testing for efficacy in living organisms. In one experiment, staphylococcus epidermidis (ATCC 12228) was harvested from a secondary working culture and grown to a concentration of approximately $1 \times 10^8$ CFU/ml. Ten colonies were incubated at 35–37° C.

for 4 hours in trypticase soy broth ("TSB"). The culture was diluted to 10 1×10$^5$ CFU/ml by serially diluting in sterile, room temperature phosphate buffered solution. Test and control groups were comprised each of fifteen 1.0 cm segments sectioned from a commercially available catheter that was not coated with any known antimicrobial compound. Ten ml of inoculum was pipetted onto each test and control segment and air dried at room temperature for 35–40 minutes. Each segment was placed in a vial containing 3.0 ml of sterile, room temperature TSB. The vials were shaker incubated (110 rpm at 35–37° C.). After 1.0 hour of incubation, five vials containing test segments and five vials containing control segments were removed. The segments were removed from each vial. Each vial was vortex mixed, on high speed, for two minutes. The TSB in each vial was sampled (1.0 ml) and serially diluted six times in sterile, room temperature phosphate buffered solution for drop counting. This process was repeated for test and control vials after 4 and 20 hours incubation.

The results are summarized in Table 2 as follows:

TABLE 2

Summary of Results, CFU/ml

| Dilution Level | Control Segments | Micro organism Concentration Incubation time | | |
|---|---|---|---|---|
| | | 1 hour | 4 hours | 20 hours |
| 1:10 | C$_1$ | TFTC | 2.0 × 10$^3$ | 6.3 × 10$^8$ |
| 1:100 | C$_2$ | TFTC | 2.0 × 10$^3$ | 6.1 × 10$^8$ |
| 1:1,000 | C$_3$ | TFTC | 1.5 × 10$^3$ | 1.0 × 10$^9$ |
| 1:10,000 | C$_4$ | TFTC | TFTC | 6.9 × 10$^8$ |
| 1:100,000 | C$_5$ | TFTC | 1.6 × 10$^3$ | 7.7 × 10$^8$ |
| Dilution Level | Treated Segments | Incubation Time | | |
| | | 1 hour | 4 hours | 20 hours |
| 1:10 | T$_1$ | TFTC | TFTC | TFTC |
| 1:100 | T$_2$ | TFTC | TFTC | TFTC |
| 1:1,000 | T$_3$ | TFTC | TFTC | TFTC |
| 1:10,000 | T$_4$ | TFTC | TFTC | TFTC |
| 1:100,000 | T$_5$ | TFTC | TFTC | TFTC |

TFTC = Too few to count (<30 CFU/ml)

These results indicated that the treated segments produced an inhibitory effect on the growth of s. epidermidis (ATCC 12228). Two routes of inhibition are possible: (1) contact inhibition, beginning with the initial inoculation of the catheter segments (either occurring in a dry environment or occurring when the coating moistened while in the TSB); or (2) while submerged in the TSB, the coating's inhibitory agent leached from the segment surface and circulated freely within the TSB.

Standard Test B2—Bio Testing with *C. albicans*

To confirm that the treated catheters are resistant to a variety of bacterial organisms, a series of tests were conducted using candida albicans, ATCC 10231. *C. albicans* was harvested from a secondary working culture and grown to a concentration of about 10$^7$ CFU/ml (20 colonies incubated in 5.0 ml TSB at 35–37° C. for 4 hours and 100 rpm). The culture was diluted to 1×10$^5$ CFU/ml by serially diluting in sterile, room temperature TSB. As described for the foregoing test with *S. epidermidis*. Test and control groups were established each having fifteen 1.0 cm segments that were sectioned from a commercially available catheter, where the test group was from a treated catheter and the control group was from an untreated catheter. Ten ml of inoculum was gently pipetted onto each test and control segment and air dried under laminar air flow for 35–40 minutes. Each segment was then placed into a sterile vial containing 3.0 ml of TSB. The vials were shaker incubated (100–110 rpm) at 35–37° C. After four hours of incubation, five vials containing test segments and five vials containing control segments were removed from incubation and the segments removed from the vials. The TSB in each vial was sampled (1.0 ml) and serially diluted four times in sterile, room temperature phosphate buffered solution ("PBS") for drop counting. The process was repeated for samples removed at 8.0 and 20.0 hours of incubation.

The data from these tests is summaried in Table 3 as follows:

| Dilution Level | Control Segments | 4 hours Incubation | 8 hours Incubation | 20 hours Incubation |
|---|---|---|---|---|
| 1:10 | C$_1$ | TFTC | TFTC | 4.1 × 10$^5$ |
| 1:100 | C$_2$ | TFTC | TFTC | 7.5 × 10$^5$ |
| 1:1,000 | C$_3$ | TFTC | TFTC | 4.1 × 10$^5$ |
| 1:10,000 | C$_4$ | TFTC | TFTC | 6.8 × 10$^5$ |
| 1:100,000 | C$_5$ | TFTC | TFTC | 1.9 × 10$^5$ |
| Dilution Level | Treated Segments | 4 hours Incubation | 8 hours Incubation | 20 hours Incubation |
| 1:10 | T$_1$ | TFTC | TFTC | TFTC |
| 1:100 | T$_2$ | TFTC | TFTC | TFTC |
| 1:1,000 | T$_3$ | TFTC | TFTC | TFTC |
| 1:10,000 | T$_4$ | TFTC | TFTC | TFTC |
| 1:100,000 | T$_5$ | TFTC | TFTC | TFTC |

TFTC = Too few to count (<30 CFU/ml)

From these data it can be concluded that the treated catheter segment had an inhibitory effect against *C. albicans* when compared to an untreated control. The experimental results indicate that the material from treated catheters does not leach when in PBS. Thus, the inoculum is inhibited upon contact with the treated catheter surface, either during the inoculum drying period or while immersed in TSB.

Standard Test B3—Bio Testing with *S. aureus* MR

*Staphylococcus aureus* (ATCC 33591) was harvested from a secondary working culture and grown to a concentration of 1×10$^8$ CFU/ml. Ten colonies were incubated for five hours in TSB at 35–37° and 100 rpm. As described above, the culture was serially diluted to obtain a culture concentration of 1×10$^5$ CFU/ml.

Fifteen test and fifteen control group catheter segments, each 1.0 cm, were sectioned from a commercially available catheter. Ten ml of the 10$^5$ inoculum was gently pipetted on each catheter segment and allowed to dry under a laminar air flow for 30–35 minutes. Each segment was placed in a sterile vial containing 3.0 ml of TSB. The vials were shaker incubated (100–110 rpm) at 35–37° C. After four hours of incubation, five vials containing test segments and five vials containing control segments were removed from the incubator. The segments were removed from the vials and the TSB was vortex mixed on high speed for 2 minutes. The TSB in each vial was sampled (1.0 ml) and serially diluted four times in sterile, room temperature PBS for drop counting. Samples were also taken after 4 and 20 hours of incubation, diluted six times and drop counted to determine organism concentration.

These data are summarized in the following Table 4:

TABLE 4

Micro Organism Concentration

| Dilution Level | Control Segments | Incubation | | |
|---|---|---|---|---|
| | | 1 hour | 4 hours | 20 hours |
| 1:10 | $C_1$ | TFTC | $7.7 \times 10^4$ | $9.5 \times 10^7$ |
| 1:100 | $C_2$ | 2333 | $6.7 \times 10^4$ | $7.3 \times 10^7$ |
| 1:1,000 | $C_3$ | 2000 | $8.1 \times 10^4$ | $6.3 \times 10^7$ |
| 1:10,000 | $C_4$ | TFTC | $7.5 \times 10^4$ | $9.5 \times 10^6$ |
| 1:100,000 | $C_5$ | TFTC | $6.8 \times 10^4$ | * |

*contamination made counting *S. aureus* colonies impossible to read

| Dilution Level | Treated Segments | 1 hour | 4 hours | 20 hours |
|---|---|---|---|---|
| 1:10 | $T_1$ | TFTC | TFTC | $8.8 \times 10^5$ |
| 1:100 | $T_2$ | TFTC | TFTC | $3.8 \times 10^4$ |
| 1:1,000 | $T_3$ | TFTC | TFTC | TFTC |
| 1:10,000 | $T_4$ | TFTC | TFTC | $2.3 \times 10^4$ |
| 1:100,000 | $T_5$ | TFTC | TFTC | $4.7 \times 10^4$ |

TFTC = Too few to count (<30 CFU/ml)

These data reveal that Applicants' method significantly reduced, but did not completely inhibit, the growth of methicillin resistant *S. aureus* (MRSA). The untreated control segments showed no sign of inhibiting the growth of MRSA.

Standard Test C—Assay of Agent Leaching

One cm catheter segments, treated with Applicants' method, were placed in five vials with 30 ml of PBS each, and shaker incubated (100 rpm) at 35–37° for 20 hours ±5 minutes. These were assayed for active ingredient with ultraviolet light ("UV") or infrared ("IR") from 200 to 1000 nm. Similarly, control catheter segments were prepared and evaluated using UV or IR. No difference between control and test spectra were observed.

In another test, five segments, each 0.5 cm long, of catheters treated with Applicants' method were vertically inserted into 20 ml ±5 ml trypticase soy agar ("TSA") inoculated with $1-2\times10^6$ CFU/ml of s. epidermidis (ATCC 12228). The petri dish containing the agar (TSA) and segments was incubated at 35–37° for 24 hours ±15 minutes in air. The area around each catheter segment was examined for reduction or inhibition of microbial growth visible in the size and/or density of colonies, i.e, the zone of inhibition ("ZOI"). The size of any area of inhibition was measured. Control samples also were established. The data obtained are summarized below in Table 5:

| Assay Part | Group | Media | Organism | Segment Numbers | | | | | |
|---|---|---|---|---|---|---|---|---|---|
| | | | | 1 | 2 | 3 | 4 | 5 | Avrg. |
| C | Test | TSA | S. epidermidis | 0.0 | 0.0 | 0.0 | 0.0 | 0.0 | 0.0 |
| D | Test | STSA | S. epidermidis | 0.0 | 0.0 | 0.0 | 0.0 | 0.0 | 0.0 |
| E | Control | TSA | S. epidermidis | 0.0 | 0.0 | 0.0 | 0.0 | 0.0 | 0.0 |
| F | Control | STSA | S. epidermidis | 0.0 | 0.0 | 0.0 | 0.0 | 0.0 | 0.0 |
| G | Test | TSA | C. albicans | 0.0 | 0.0 | 0.0 | 0.0 | 0.0 | 0.0 |
| H | Test | STSA | C. albicans | 0.0 | 0.0 | 0.0 | 0.0 | 0.0 | 0.0 |
| I | Control | TSA | C. albicans | 0.0 | 0.0 | 0.0 | 0.0 | 0.0 | 0.0 |
| J | Control | STSA | C. albicans | 0.0 | 0.0 | 0.0 | 0.0 | 0.0 | 0.0 |

Wherein *S. epidermidis* is ATCC 12228; STSA is soft trypticase soy agar and *C. albicans* is ATCC 10231.

The ZOI screening test produced no visible reduction in density of colonial growth of either *S. epidermidis* or *C. albicans* after 24 hours of exposure.

The spectrometry and ZOI evidence indicates that substantial leaching of active compound from the treated catheters does not occur. Accordingly, Applicants' invention allows beneficial bacteria to exist in biological systems but does not permit the growth of bacteria on treated surfaces. Further, because the active compound does not leach, Applicants' method operates to permanently impart the antimicrobial characteristic to the treated surface.

EXAMPLE TWO

Quaternary Ammonium Salt IPN Polymer on Silicone Catheters

In another set of experiments, Applicants evaluated various solvent mixes to determine the degree of swelling of commercially available silicone catheters. The purpose of these experiments was to identify solvent blends that would result in excess of 25–30% weight gain after a 5 minute immersion. Thirty percent or more weight gain has been deemed the weight gain reflecting optimization of adequate penetration of the solvent (and the quaternary ammonium salt dissolved in the solvent) into a silicone rubber matrix. The swelling results are shown below in Table 6 using a commercially available silicone rubber catheter:

| Solvent Mixture | Approximate Immersion Time, Min. | % Wt. Gain |
|---|---|---|
| 75 methanol | | |
| 25 THF / 75 methanol | 0.25 | 6.3 |
| 25 THF / 50 methanol | 5.0 | 6.3 |
| 50 THF / 25 methanol | 5.0 | 24.6 |
| 75 THF / 0 methanol | 5.0 | 52.3 |
| 100 THF | 5.0 | 85.1 |

Applicants used 25 methanol/75 THF solution and approximately 52% weight gain for these experiments. Again, catheters were exposed to a 5% solution of quaternary ammonium salt in 25 methanol/75 THF followed by 5 minute exposure to 0.1N NaOH, approximately 30 minutes to an hour air drying, followed by forced air drying.

Standard Test A—Bromophenol Blue Testing

The bromophenol blue test was used on the treated silicone catheter which indicated the presence of the impregnants by the surface of the treated catheter turning blue. As with the polyurethane catheter, the silicone catheter was given a 5×series of rinsings in 140° F. hot water of 3 minutes at approximately 200:1 on a shaker with vigorous agitation. Retesting with bromophenol blue dye indicated that the polymerized quaternary ammonium salt was not extracted from the body of the catheter.

Standard Test B—Bio Testing of Silicone Catheter Segments

Samples of untreated silicone catheter (control) and a treated catheter were evaluated against *S. epidermidis*. The challenge organism, *S. epidermidis*, was harvested and standardized to $1\times10^8$ CFU/ml. The suspension was diluted to approximately $1\times10^5$ CFU/ml. Several one cm pieces of each type of catheter were inoculated with 0.01 ml of the $10^5$ CFU/ml suspension to give a final inoculum of $1\times10^3$ CFU per piece. Each piece was allowed to dry in a sterile dish for approximately 10 minutes and then placed in a vial containing 3 mls of TSB. The vials were incubated at 32–35° C. for two days and evaluated for growth. The treated catheters killed the challenge organism. By challenging the TSB from the vials showing no growth without the catheters, Applicants demonstrated that the treated catheters did not leach the antimicrobial agent.

Additional silicone catheter segments were tested for ZOI against *S. epidermidis, S. aureus* and *C. albicans* with no evidence of leaching. The results are shown below in Table 7:

| Catheter Sample Identification | S. epidermidis | S. aureus | C. albicans |
|---|---|---|---|
| Silicone rubber control | 0.0 | 0.0 | 0.0 |
| Treated silicone rubber catheter | 0.0 | 0.0 | 0.0 |

Although Applicants' experiments focused on the application of Applicants' method to catheters, it is readily apparent to those skilled in the art, that other polymeric surfaces, particularly those present in medical devices, may be subjected to Applicants's method.

Standard Test C—In Vivo Bio Testing of Silicone Catheter Segments

In one experiment, a silicone catheter was prepared as described above using a 5% solution of quaternary ammonium salt in toluene solvent and followed by polymerization using 0.1N NaOH as a catalyst and heat to remove residual solvent. This treated catheter was implanted in a rabbit to determine whether Applicants' method, when applied to a catheter, inhibits bacterial growth following active challenge with an organism at the site of implant. The treated catheter was implanted subcutaneously and *S. aureus* in a volume of 50 μl was deposited at the site. A control catheter was implanted in another animal. After 15 days of implantation, the treated and untreated catheters were removed, streaked across an agar plate, incubated and the colonies were counted. The colonies generated by the untreated catheter were too numerous to count (greater than 100) while only seven colonies were generated by the treated catheter. The test protocol and test results reflect the effectiveness of treating catheters with a polymerized quaternary ammonium salt.

As the foregoing experiments demonstrate, Applicants' method can be used to create a catheter having non-leaching, antimicrobial properties. Imparting such a characteristic to a catheter that has leaching antimicrobial properties, e.g., one that has antibiotics impregnated therein, may result in a catheter that is able to address an existing systemic infection that may affect the catheter surface. Applicants' process does not preclude the addition of antibiotics as a coating surface. Thus antibiotics can be used in conjunction with a surface that has been treated according to Applicants' method.

Although Applicants' experiments focused on the application of Applicants' method to catheters, it is understood that other polymeric surfaces, particularly those present in medical devices and supplies, may be subjected to Applicants' method.

EXAMPLE THREE

IPN in Porous Substrates

Another embodiment of Applicants' method does not require the host polymer substrate be capable of being swelled in a solvent. In this embodiment, the quaternary salt monomer/solvent mixture is allowed to penetrate the pores or interstices of the host polymer or substrate, the solvent is evaporated and the quaternary ammonium salt monomer is polymerized in situ. Polymerization is accomplished by heat, 0.1N NaOH, 0.1N HCl or a combination thereof. This results in an IPN in which the quaternary salt polymer is entangled in the pores of the host polymer or substrate. Applicants have used their method in host polymers having pores of approximately 2 microns. The host substrate can be a polymer such as Teflon or a variety of plastic or sponge-like materials such as foams and includes natural products such as paper. Using this procedure the quaternary salt polymer/host polymer IPN is highly stable and exhibits permanence as evidenced by (1) resistance to 5×hot water rinses for three minutes at 140° F. and (2) resistance to up to 10 autoclave cycles for 30 minutes at 270° F. In each case, the blue dye test demonstrate the presence of the quaternary ammonium salt polymer after exposure to the elevated temperature.

EXAMPLE FOUR

IPN Coating

Further, it is apparent that Applicants' method may be used to create a polymeric IPN coating that can be applied to other solid substrates, including, but not limited to, substrates made of metal and plastic. For example, a polymerizable quaternary ammonium salt monomer at approximately 5% concentration, based on the resin solids, may be added to a commercially available coating system. The coating, with the quaternary salt, may then be applied, e.g., by brushing or spraying, to the metallic surface to be coated. As the coating dries, the quaternary salt provided by Applicants method simultaneously polymerizes. Using this method Applicants successfully treated copper, aluminum, steel and stainless steel, but it is understood that other solid substrate surfaces, e.g., wood and plastic, can be treated. Blue dye testing verified the presence of the polymerized quaternary ammonium salt polymer in the coating system when the coating system was an epoxy paint.

What is claimed is:

1. A method of imparting antimicrobial properties to a polymeric substrate comprising:

providing a polymerizable or monomeric quaternary ammonium salt in a solvent;

contacting the polymeric substrate to said solvent containing said quaternary salt;

permitting said quaternary salt to be absorbed by the polymeric substrate; and polymerizing said quaternary salt such that an interpenetrating polymer network is formed with said polymeric substrate.

2. A method according to claim 1 wherein said quaternary salt has the general formula of:

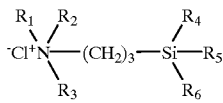

3. A method according to claim 2 wherein $R_1$ and $R_2$ are methyl groups, $R_3$ is octadecyl, and $R_4$, $R_5$ and $R_6$ are methoxy groups.

4. A method according to claims 1, 2 or 3 wherein said polymerization of said quaternary ammonium salt is achieved by exposing it to 0.1N NaOH, 0.1N HCl, heat or a combination thereof.

5. A method according to claims 1, 2 or 3 wherein said solvents for said quaternary ammonium salt rapidly swell said polymeric substrate to a degree necessary to achieve sufficient penetration of said polymeric substrate to ensure fixation therein while retaining the functional characteristics of said polymeric substrate.

6. A method accordingly to claim 5 wherein said solvent results in the desired degree of swelling of said polymeric substrate in less than ten minutes.

7. A method according to claim 5 wherein said solvent is ethyl acetate, a mixture of tetrahydrofuran, and methanol, or any organic solvent for said quaternary ammonium salt that swells said polymeric substrate.

8. A method according to claim 5 wherein said solvent is 75THF/25MEOH, petroleum ether, toluene, methyl ethyl ketone (MEK), acetone, dimethoxy dimethyl silicone, mineral spirits, dimethyl acetamide (DMA) or dimethyl formamide (DMF), for said quaternary ammonium salt that swells said polymeric substrate.

9. A method for creating a catheter having non-leaching, antimicrobial properties comprising: providing a polymerizable or monomeric quaternary salt in a solvent; providing a catheter; and contacting said catheter to said solvent containing said quaternary salt such that said quaternary salt polymerizes within and upon the catheter in situ.

10. A method according to claim 9 wherein said quaternary salt has the general formula of:

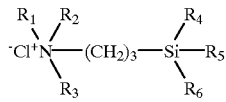

11. A method according to claim 10 wherein $R_1$ and $R_2$ are methyl groups, $R_3$ is octadecyl, and $R_4$, $R_5$ and $R_6$ are methoxy groups.

12. A method according to claims 9, 10 or 11 wherein said polymerization of said quaternary salt is achieved by exposing it to 0.1N NaOH, 0.1N HCl, heat or a combination thereof.

13. A method according to claims 9, 10 or 11 wherein said solvents for said quaternary ammonium salt rapidly swell said catheter approximately 20–50 percent by weight in approximately 10 minutes or less while retaining the functional characteristics of said catheter.

14. A method according to claim 13 wherein said solvent is ethyl acetate, a mixture of tetrahydrofuran and methanol, or any organic solvent for said quaternary ammonium salt that swells said catheter.

15. A method according to claim 9 wherein said catheter is made of silicone, polyurethane, thermoplastic or plastic.

16. A method according to claim 9 wherein said catheter is impregnated with antibiotics.

17. A method for creating a non-leaching, biocompatible, antimicrobial, polymeric coating comprising: providing a polymerizable or monomeric quaternary salt in a solvent; exposing a substrate having interstices in which said quaternary salt can be absorbed and polymerized; permitting said quaternary salt to be absorbed by the substrate; and polymerizing said quaternary salt such that an interpenetrating polymer network is formed within the interstices of the substrate.

* * * * *